United States Patent [19]
Gadsby

[11] Patent Number: 5,456,710
[45] Date of Patent: Oct. 10, 1995

[54] VENTED ELECTRODE

[75] Inventor: Peter D. Gadsby, Duvall, Wash.

[73] Assignee: Physio-Control Corporation, Redmond, Wash.

[21] Appl. No.: 268,629

[22] Filed: Jun. 30, 1994

[51] Int. Cl.⁶ .................................................. A61N 1/04
[52] U.S. Cl. ........................................ 607/142; 607/153
[58] Field of Search ................................... 607/142, 152, 607/153

[56] References Cited

U.S. PATENT DOCUMENTS

| | | | |
|---|---|---|---|
| 3,702,613 | 11/1972 | Panico et al. | 128/417 |
| 3,762,420 | 10/1973 | Moore et al. | 128/417 |
| 4,300,575 | 11/1981 | Wilson | 128/798 |
| 4,367,755 | 1/1983 | Bailey | 128/798 |
| 4,776,350 | 10/1988 | Grossman et al. | 128/799 |
| 4,779,630 | 10/1988 | Scharnberg et al. | 128/783 |
| 4,974,917 | 12/1990 | Kornerup | 128/798 |
| 4,979,517 | 12/1990 | Grossman et al. | 128/798 |
| 4,998,536 | 3/1991 | Scharnberg | 128/800 |

*Primary Examiner*—William E. Kamm
*Attorney, Agent, or Firm*—Christensen, O'Connor, Johnson & Kindness

[57] ABSTRACT

Disclosed is an electrode (10, 60) for placement upon the skin of a patient (12) to deliver electrical pulses from medical electronic equipment (16) to the patient. The electrode includes (10, 60) an electrically conductive layer (24, 74) having a skin-facing side and an upper side. An impedance-decreasing layer (32, 82) is adjacent a substantial portion of the skin-facing side of the conductive layer (24, 74). A substantially electrically nonconductive backing layer (18, 68) is adjacent the upper surface of the conductive layer (24, 74), the backing layer (18, 68) being substantially impermeable to the impedance-decreasing layer (32, 82). A gas-permeable layer (20, 70) is between the backing layer (18, 68) and the conductive layer (24, 74). Finally, a vent (22, 72) is provided for venting gas formed between the impedance-decreasing layer (32, 82) and the conductive layer (24, 74) to the environment.

18 Claims, 4 Drawing Sheets

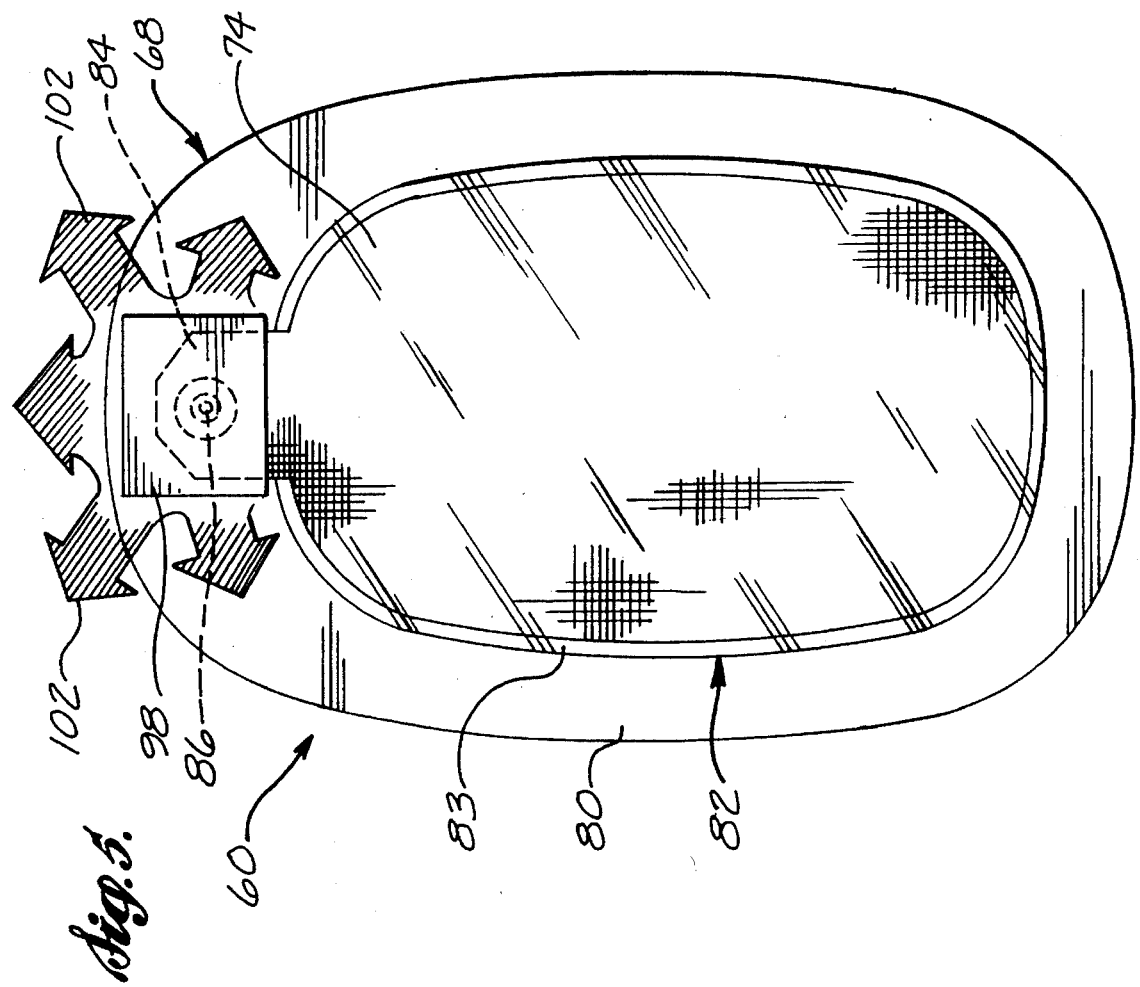
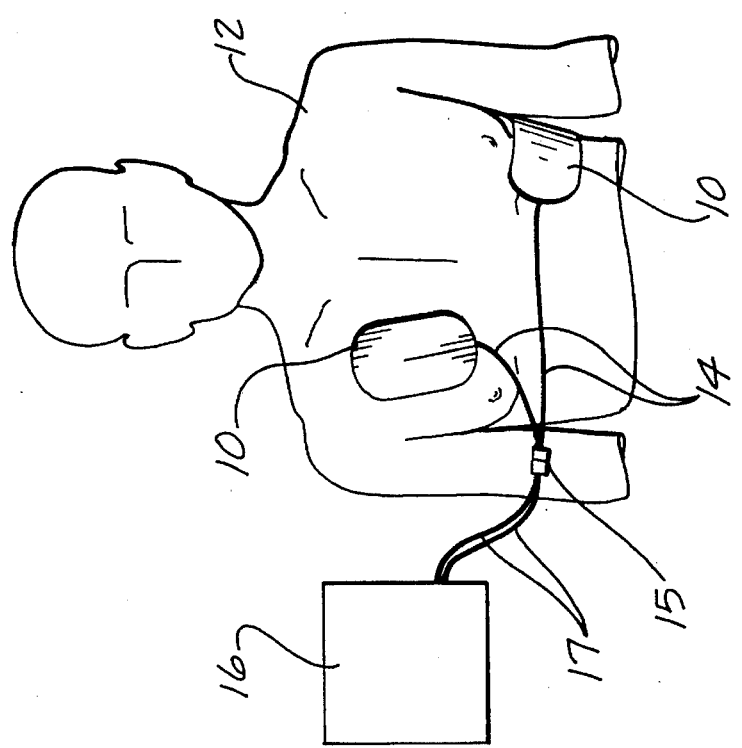

VENTED ELECTRODE

FIELD OF THE INVENTION

The present invention relates generally to electrodes, and more particularly to electrodes used for delivery of electrical pulses to a patient for medical treatment.

BACKGROUND OF THE INVENTION

Electrodes are used to connect medical electronic equipment to patients. One type of medical electronic equipment frequently attached to a patient is stimulation equipment. Stimulation equipment has several different uses, such as stimulating a patient's heart to beat (defibrillation), stabilizing the heart beat of a patient (cardiac pacing), transcutaneous nerve stimulation for pain control and other uses. The stimulation equipment delivers one or more electrical pulses via the electrodes to the skin of the patient.

Most electrodes used with medical electronic equipment incorporate an electrically conductive, impedance-decreasing gel disposed between a flexible conductive plate and the patient's skin. Typically, the conductive plate is made of a metal foil, such as a tin alloy, or a conductive plastic impregnated with carbon. The gel serves to ensure good electrical contact between the patient and the plate, and to adhere the electrode to the patient's skin. The non-skin-facing side of the plate is generally covered with an electrically insulating backing layer. Usually, a post electrically coupled to the plate, projects from the insulating backing layer. Wire is connected to the post from the medical electronic equipment for supplying electrical pulses to the electrode.

A problem with the use of such gels is that the electrical pulses transmitted through the electrode to the patient's skin causes hydrolysis of the gel. The problem is exacerbated with medical stimulation equipment used for defibrillation or cardiac pacing because these types of stimulation equipment usually deliver higher voltages and currents to the patient, which increases the rate of hydrolysis. For example, defibrillation equipment typically delivers up to 5,000 volts to the patient at a maximum current of 60 amps. Cardiac pacing equipment commonly delivers up to 300 volts to the patient at a maximum current of 0.2 amps.

The hydrolysis produces hydrogen and oxygen gas, which tends to accumulate between the gel and the flexible metal plate and creates two primary effects that are undesirable. First, the accumulation of the gases generally decreases the conductivity between the electrode and the patient.

Second, the decrease in conductivity is not uniform across the surface of the electrode. The gas commonly accumulates in pockets, such that the conductivity between the electrode and the patient substantially decreases in areas of the electrode that are separated from contact with the patient by a gas pocket. To maintain the same current flow to the patient an increased current flow occurs in other areas of the electrode where conductivity has not been decreased. The increase in current flow in other areas of the electrode increases the current density in these areas. If the density of current flow increases enough in these areas, patient discomfort results. If the current density increases even further, burning of the patient's skin may result. The problem is exacerbated with electrodes designed for pediatric use because these electrodes tend to be smaller, yet have current flows comparable to electrodes used for adults.

There is a continuing need for a solution to these problems. U.S. Pat. No. 4,300,575 discloses an electrode including air-permeable components so that the patient's skin can "breathe" through the electrode. U.S. Pat. No. 4,367,755 discloses an electrode including a multiplicity of perforations formed therethrough, such that moisture absorbed by the electrode from the patient's skin may be dissipated through the perforations.

While perhaps satisfactory for some uses, the electrodes disclosed in the above two patents are generally unsatisfactory to solve the problem caused by hydrolysis of the gel as described above. Specifically, in the electrodes disclosed in U.S. Pat. Nos. 4,300,575 and 4,367,755, electrically conductive gel can pass through the perforations, or through the gas-permeable layers to the upper surface of the insulating backing, which results in an electrical hazard to medical personnel.

More particularly, medical personnel treating the patient could inadvertently come into contact with gel on the upper side of the insulating layer and be electrically shocked. This problem is of special importance with electrodes used for cardiac pacing or defibrillation because of the higher electrical voltages and currents used with these types of electrodes. In general, it is inadvisable for medical personnel to physically contact a patient who is undergoing cardiac pacing or defibrillation with externally applied electrodes. Nonetheless, gel present on the upper side of the insulating layer of the electrodes creates an even greater hazard because the gel tends to make a good electrical connection between the electrode and anything that contacts the gel.

Accordingly, the present invention provides a solution to the above described problems.

SUMMARY OF THE INVENTION

The present invention provides an electrode for placement upon the skin of a patient to deliver electrical pulses from medical electronic equipment to the patient. The electrode includes an electrically conductive layer having a skin-facing side and an upper side. An impedance-decreasing layer is adjacent a substantial portion of the skin-facing side of the conductive layer. A substantially electrically nonconductive backing layer is adjacent the upper surface of the conductive layer, the backing layer being substantially impermeable to the impedance-decreasing layer. Finally, a vent is provided for venting gas formed between the impedance-decreasing layer and the conductive layer to the environment.

In a preferred embodiment, the conductive layer is permeable to gases. Gas permeability of the conductive layer may be achieved in a number of ways, such as by perforating the conductive layer, or forming the conductive layer from a mesh, or by using a conductive ink printed on a porous material.

In one embodiment, venting is achieved by providing a gas-permeable layer between the conductive layer and the backing layer. Gas formed between the impedance-decreasing layer and the conductive layer travels through the conductive layer and into the gas-permeable layer in this preferred embodiment. A portion of the gas-permeable layer extends beyond the periphery of the impedance-decreasing layer. Thus, gas collected in the gas-permeable layer can vent to the environment from the portion of the gas permeable layer, which extends beyond the periphery of the impedance-decreasing layer.

In an alternate embodiment, a gas-permeable layer between the conductive layer and the backing layer is not required. In this alternate embodiment, both the conductive layer and the backing layer are permeable to gases. Thus, gas formed between the impedance-decreasing layer and the conductive layer can pass through the conductive layer and vent to the environment through the backing layer. However, the backing layer is substantially impermeable to the impedance-decreasing layer so as to not increase the risk of electrical hazard to medical personnel treating the patient.

In other aspects of the invention, electrical coupling between the conductive layer and the skin of the patient substantially only occurs through the impedance-decreasing layer. Further, electrical coupling of the conductive layer to medical electronic equipment substantially occurs through a connection that is devoid of the impedance-decreasing layer to inhibit galvanic corrosion.

In yet other aspects of the invention, the conductive layer does not need to be gas-permeable. Instead, channels or creases are formed in the conductive layer, which collect gas formed between the impedance-decreasing layer and the conductive layer. The channels direct the gas to a vented portion of the electrode, such as an area extending beyond the periphery of the impedance-decreasing layer.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a schematic view of a pair of electrodes in accordance with the present invention in place on a patient's upper torso;

FIG. 5 is a view of the electrode of FIG. 4, from the patient-facing side of the electrode.

DETAILED DESCRIPTION OF THE PREFERRED EMBODIMENTS

Figure 2:
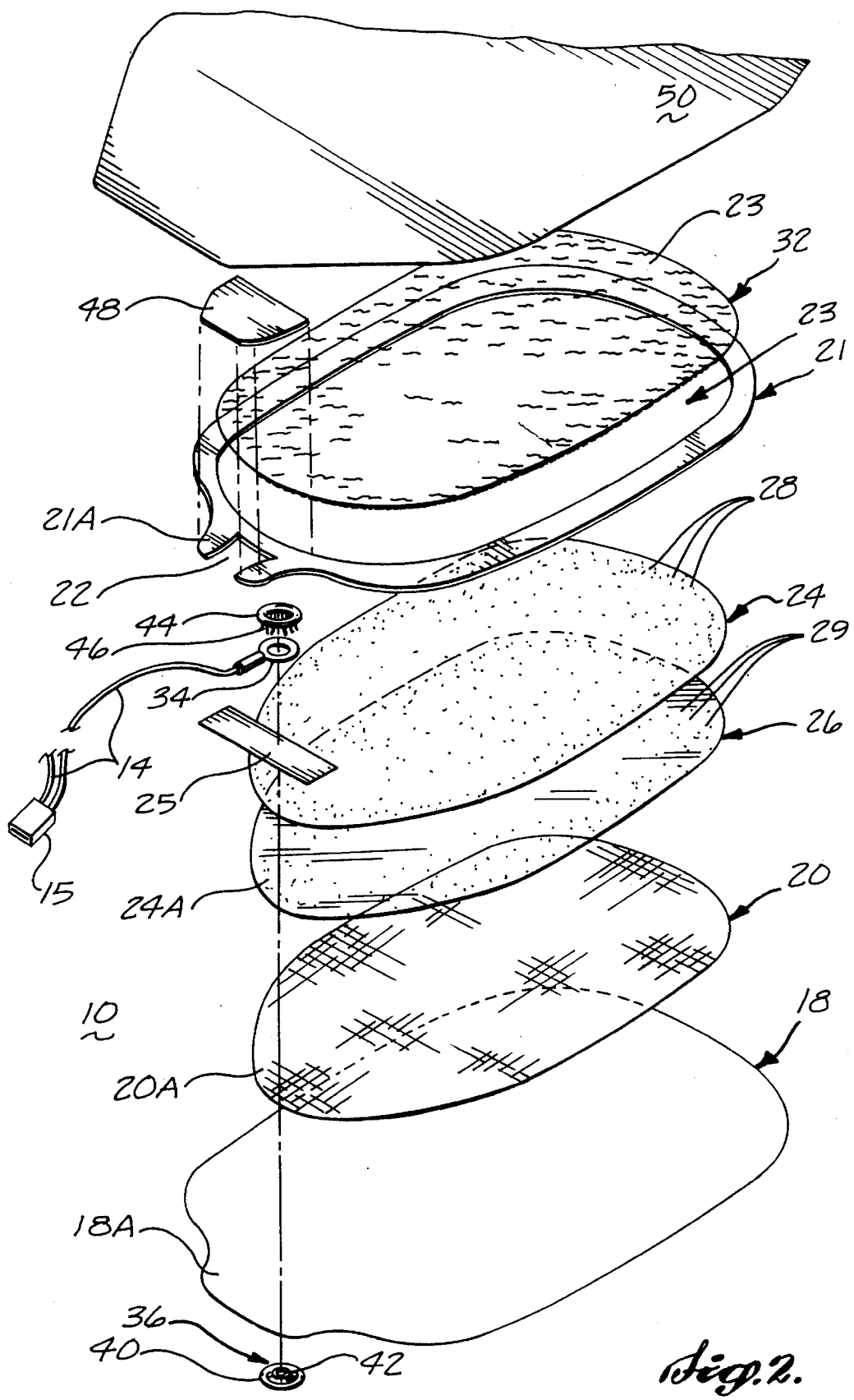
FIG. 2 is an isometric exploded view of one of the electrodes of FIGS. 1, including a protective liner.

Referring to FIG. 1, a pair of electrodes 10 formed in accordance with the present invention are placed on a patient 12. As shown, the electrodes 10 are generally placed on the front surface of the patient's upper torso. Lead wires 14 from the electrodes 10 terminate in a connector 15. The connector 15 electrically couples lead wires 14 to lead wires 17 from medical electronic equipment 16. The medical electronic equipment 16 provides electrical pulses to the electrodes 10 for treatment of the patient 12.

An exploded view of an electrode 10 is shown in FIG. 2. Electrode 10 includes several layers of material. Generally flat backing layer 18 is the first layer opposite the patient-facing side of electrode 10. In the illustrated embodiment, backing layer 18 is generally oval in shape, but having one of the ends that is along the major axis of the oval-shape elongated. Backing layer 18 is formed from a thin, flexible, nonwetable material that is substantially electrically nonconductive. One type of suitable material for forming backing layer 18 is polyethylene foam.

Gas-permeable layer 20 is adjacent backing layer 18. In this illustrated embodiment, gas permeable layer 20 has a more-or-less oval shape. The length of the oval is slightly less than the length of backing layer 18, and the width of the oval is significantly less than the width of backing layer 18. Gas permeable layer 20 is adhered more-or-less centrally to the main body-portion of backing layer 18, preferably with a hypoallergenic acrylic adhesive.

Materials suitable for forming gas-permeable layer 20 include any material that is substantially permeable to gases, which can be formed into a thin, flexible sheet. Examples of such materials are nonwoven materials, an open cell foam, or a plastic mesh. Nonwoven polyester has been found suitable for practicing the present invention. A source of suitable nonwoven polyester is the Avery Dennison company of Painesville, Ohio. In particular, nonwoven polyester having a weight of approximately 1.4 oz per square yard, sold by Avery Dennison, has been found satisfactory for forming gas-permeable layer 20.

A conductive layer 24, having a shape substantially identical to gas-permeable layer 20, is between the patient-facing side of gas-permeable layer 20 and patient 12. Conductive layer 24 may be made of any thin, flexible material that is a good electrical conductor, such as metal foil, a conductive plastic impregnated with carbon, a conductive ink imprinted on a plastic, or other similar materials.

Preferably, conductive layer 24 is formed as described in U.S. Pat. No. 4,979,517, which is hereby incorporated by reference. Namely, conductive layer 24 is preferably formed of tin foil, comprising at least 99.98% tin, having a thickness of approximately 2 mils. As described in U.S. Pat. No. 4,979,517, a conductive layer formed in this way is thin, and therefore susceptible to damage during manufacture of an electrode 10. Hence, a support sheet 26, having a shape substantially identical to conductive layer 24, is preferably adhered to the non-patient-facing side of the conductive layer 24 to increase the durability of conductive layer 24 during manufacture of electrode 10. Support sheet 26 may be made of any thin flexible material that is tear resistant. Preferably, support sheet 26 is formed of 1-mil polyester, and is adhered to conductive layer 24 with a hypoallergenic acrylic adhesive.

Conductive layer 24 is made permeable to gases as follows. A plurality of regularly, spaced-apart bore holes 28 are formed generally perpendicular through the surface of conductive layer 24. Bore holes 28 preferably have a diameter of approximately 0.015", and a bore hole is preferably no more than 0.120" away from another bore hole. Corresponding bore holes 29 are formed in the support sheet 26.

The preferred method of making electrode 10 is to first adhere support sheet 26 to a conductive sheet 24. After this, gas-permeable sheet 20 is adhered to the side of the support sheet opposite the conductive sheet, then the bore holes 28 and 29 are formed through the assembly. Preferably, the adhesive used is a hypoallergenic acrylic. From this assembly, conductive layer 24, support sheet 26 and gas-permeable layer 20 are cut out with a die as an assembled unit, such that each of these layers have a substantially identical shape. Then gas-permeable layer 20 of this above assembly is adhered to backing layer 18 as previously described.

A ring layer 21 is adhered to backing layer 18 over conductive layer 24. Ring layer 21 may be made of any thin, flexible material, that is substantially electrically nonconductive. Preferably ring layer 21 is made of the same material comprising backing layer 18. Ring layer 21 is for providing smoother contact of electrode 10 with patient 12.

Ring layer 21 includes an external periphery, which defines a shape corresponding generally to the shape of backing layer 18, including the elongated end of backing layer 18. The elongated end of ring layer 21 includes an open, cutout dovetail region 22, with the longer base of the dovetail being approximately perpendicular to the longitudinal axis of the oval. The internal periphery of ring layer 21 defines an open central region 23, generally being oval in shape.

Figure 3:
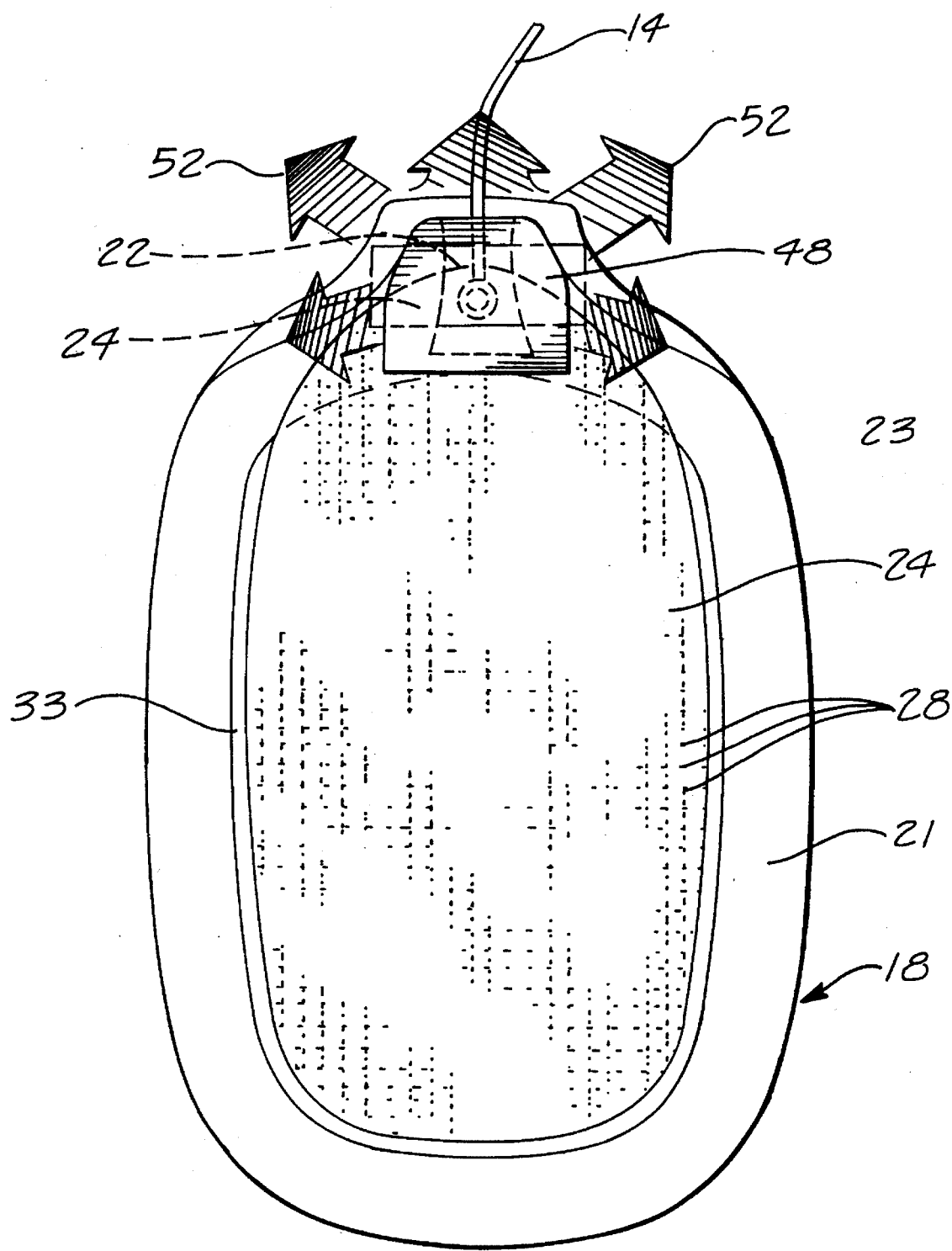
FIG. 3 is a view of one of the electrodes of FIG. 1, from the patient-facing side of the electrode.

FIG. 3 is a view of an electrode 10 from the patient-facing side of electrode 10. Referring to FIG. 3, ring layer 21 is positioned more-or-less centrally upon backing layer 18, overlaying conductive layer 24. The open central region 23 of ring layer 21 contains the major portion of conductive layer 24. Specifically, the open central region 23 of ring layer 21 substantially surrounds the outer periphery of conductive layer 24, except for one longitudinal end of conductive layer 24. More particularly, this longitudinal end of conductive layer 24 extends between dovetail region 22 of ring layer 21 and backing layer 18.

Returning to FIG. 2, a rectangular length of conventional polyester tape 25 is preferably between ring layer 21 and conductive layer 24. Tape 25 is positioned between dovetail region 22 of ring layer 21, and conductive layer 24. Tape 25 is placed such that its longitudinal axis is approximately bisected, generally perpendicularly, by the major axis of the oval-shape defined by conductive layer 24. Tape 25 is preferably a double-sided adhesive type, and of a length sufficient to extend to opposite edges of conductive layer 24. Additionally, the tape adhesive is preferably a hypoallergenic acrylic.

In this preferred embodiment, the entire patient-facing side of backing layer 18 is coated with a hypoallergenic acrylic adhesive, while the non-patient-facing side of ring layer 21 is not coated with an adhesive. Thus, ring layer 21 adheres to the portion of the backing layer 18, where ring layer 21 and backing layer 18 contact one another. However, there is not any adhesive to adhere the elongated end of ring layer 21 to conductive layer 24. Hence, the double-sided adhesive tape 25 helps to adhere the elongated end of ring layer 21 to conductive layer 24. Further, as described herein in more detail, tape 25 helps to ensure against galvanic corrosion.

Referring to FIG. 1, lead wire 14 is of conventional type multistrand wire, having a gauge appropriate to the current and voltage being supplied by medical electronic equipment 16. Each lead wire 14 includes a distal end that connects to a lead wire 17 from medical electronic equipment 16. Preferably, the connection between a lead wire 17 and a lead wire 14 is made with a conventional, quick-type electrical connector 15, which securely electrically couples lead wires 14 and lead wires 17 together.

As shown in FIG. 2, the proximal end of a lead wire 14 terminates in a standard ring lug 34, of a well known type for connecting an end of a wire to a post. Ring lug 34 is positioned adjacent tape 25, approximately opposite dovetail region 22 of ring layer 21, with lead 14 extending more-or-less radially out of dovetail region 22. Preferably, ring lug 34 and lead wire 14 are electrically connected to conductive layer 24 with a prong ring 44. Prong ring 44 includes a plurality of inwardly projecting teeth 46, that are bent at an angle to project towards the conductive layer 24. Teeth 46 penetrate through ring lug 34, tape 25, conductive layer 24, support sheet 26, dovetail region 22 and backing layer 18.

When teeth 46 have penetrated through these items, teeth 46 engage a socket 36 positioned adjacent the non-patient-facing side of backing layer 18. Socket 36 is formed with a rim 40 surrounding a central column 42 that projects generally perpendicular against backing layer 18. Teeth 46 extend through backing layer 18 and project into the space between rim 40 and column 42, wherein teeth 46 are bent outward and downward. When teeth 46 are bent outward and downward, rim 40 of socket 36 is clamped snugly between teeth 46 and the annular outer portion of prong ring 44.

Further, backing layer 18, gas-permeable layer 20, support sheet 26, conductive layer 24 tape 25, and ring lug 34 are all clamped securely between prong ring 44 and socket 36. Preferably socket 36 and prong ring 44 are formed of cartridge brass and coated with tin.

Insulative pad 48 is disposed adjacent the elongated end of ring layer 21, wherein insulative pad 48 covers dovetail region 22 of ring layer 21, and prong ring 44. Insulative pad 48 generally corresponds in shape to the elongated end of ring layer 21, having edges approximately coextensive therewith. Preferably, insulative pad 48 does not cover any portion of central region 23 of ring layer 21. Insulative pad 48 may be made of any thin, flexible material of high dielectric strength, such as polyethylene foam. Preferably, insulative pad 48 is adhered to electrode 10 with a hypoallergenic acrylic adhesive. Additionally, preferably the patient-facing side of insulative pad 48 is coated with a hypoallergenic acrylic adhesive to aid in adhering electrode 10 to patient 12.

The purpose of insulative pad 48 is to prevent burning of the patient's skin in the event that prong ring 44 becomes electrically disconnected from conductive layer 24. More particularly, metal foil comprising conductive layer 24 could break away from the teeth 46 of prong ring 44, teeth 46 could break away from prong ring 44, or some other occurrence could cause prong ring 44 to become electrically disconnected from conductive layer 24. In which case, if insulative pad 48 was not included with electrode 10 as described above, all of the electric current from medical electronic equipment 16 would flow into patient 12 through the relatively small area bounded by prong ring 44, resulting in a high current density and likely burning of patient 12. Insulative pad 48 protects against this occurrence.

As shown in FIG. 2, an impedance-decreasing layer 32 is applied to the portion of conductive layer 24 facing patient 12 through central region 23 of ring layer 21. Impedance-decreasing layer 32 aids in decreasing the impedance between conductive layer 24 and patient 12 to ensure good electrical contact. Impedance-decreasing layer 32 preferably comprises a conventional conductive gel formed from a gel matrix, an electrolyte and water. A source of such conductive gels are those manufactured by the LecTec Corporation of Minnetonka, Minn. Another gel suitable for use in practicing the present invention is the gel disclosed in U.S. Pat. No. 4,979,517, which patent was previously incorporated herein by reference.

When an electrical current is passed through dissimilar metals in the presence of an electrolyte, galvanic corrosion may result. Tape 25, insulative pad 48, and ring layer 21 help to ensure that the impedance-decreasing layer 32, which preferably comprises an electrolyte, does not come into contact between prong ring 44 and conductive layer 24 to prevent galvanic corrosion.

Electrodes 10 are packaged with a protective liner 50 as shown in FIG. 2 (the protective liner 50 is not shown in FIGS. 1 and 3). Protective liner 50 is releasably attached to electrode 10. More particularly, protective liner 50 includes a smooth surface which overlies the entire patient-facing side of electrode 10 to protect the patient-facing surfaces from contaminants. When electrode 10 is used, protective liner 50 is peeled away from the patient-facing side of electrode 10, prior to placing electrode 10 on the patient's skin.

In practice, electrode 10 is pressed against patient 12, after protective liner 50 has been removed, with impedance-decreasing layer 32 adjacent patient 12. Impedance-decreasing layer 32 is gummy and thus aids in adhering electrode 10 to the patient 12. Further, the patient-facing side of ring layer 21 and the patient-facing side of insulative pad 48 are preferably coated with a hypoallergenic acrylic adhesive. This also helps in adhering electrode 10 to patient 12.

Electrodes 10 are generally used in pairs as shown in FIG. 1. One electrical lead 14 attaches to one of electrodes 10, and another electrical lead attaches to the other electrode 10. If impedance-decreasing layer 32 begins to hydrolyze when an electric current is applied to electrodes 10, the bubbles of gas vent through holes 28 and 29, respectively formed in conductive layer 24 and support sheet 26. This prevents the bubbles from forming pockets of gas between conductive layer 24 and patient 12. Thus, good electrical contact is maintained between electrode 10 and patient 12.

From holes 28 and 29, the bubbles enter gas-permeable layer 20, whereupon the bubbles vent to the environment through the end of gas-permeable layer 20 that extends under ring layer 21. The reason is because the minor axis of conductive layer 24 is shorter than the minor axis of open central region 23 of ring layer 21 as shown in FIG. 3. Thus, an annular strip 33 is disposed between a substantial portion of the inner periphery of ring layer 21, and the outer periphery of conductive layer 24. When conductive layer 24 is coated with impedance-decreasing layer 32, annular strip 33 fills with impedance-decreasing layer 32. Since impedance-decreasing layer 32 has a width greater than the width of gas-permeable layer 20, bubbles generally cannot escape from the edge of gas-permeable layer 20 in areas that border on annular strip 33. In other words, the impedance-decreasing layer 32 tends to seal the edges of gas-permeable layer 20.

However, the portion of gas-permeable layer 20 that extends under ring layer 21 does not border on annular strip 33. Thus, the bubbles vent through this portion of gas-permeable layer 20 as indicated by the arrows 52 in FIG. 3.

In an alternate embodiment, backing layer 18 is formed from a nonwetable, hydrophobic gas-permeable layer that is substantially electrically nonconductive, and impermeable to liquids and/or gels. Thus, gas formed from hydrolysis of impedance-decreasing layer 32 can escape through backing layer 18, but impedance-decreasing layer 32 cannot penetrate therethrough. Hence, there is little danger that medical personnel treating patient 12 would inadvertently come into contact with impedance-decreasing material on the non-patient-facing side of backing layer 18. Therefore, there is no increase in the danger of accidental electrical shock to medical personnel when using an electrode in accordance with the alternate embodiment, wherein the electrode provides the advantage of venting gas caused by hydrolysis.

In the alternate embodiment, gas-permeable layer 20 would preferably be eliminated. More specifically, gas would vent directly through backing layer 18, rather than entering gas-permeable layer 20, and venting through peninsula portion 22 of gas-permeable layer 20.

Figure 4:
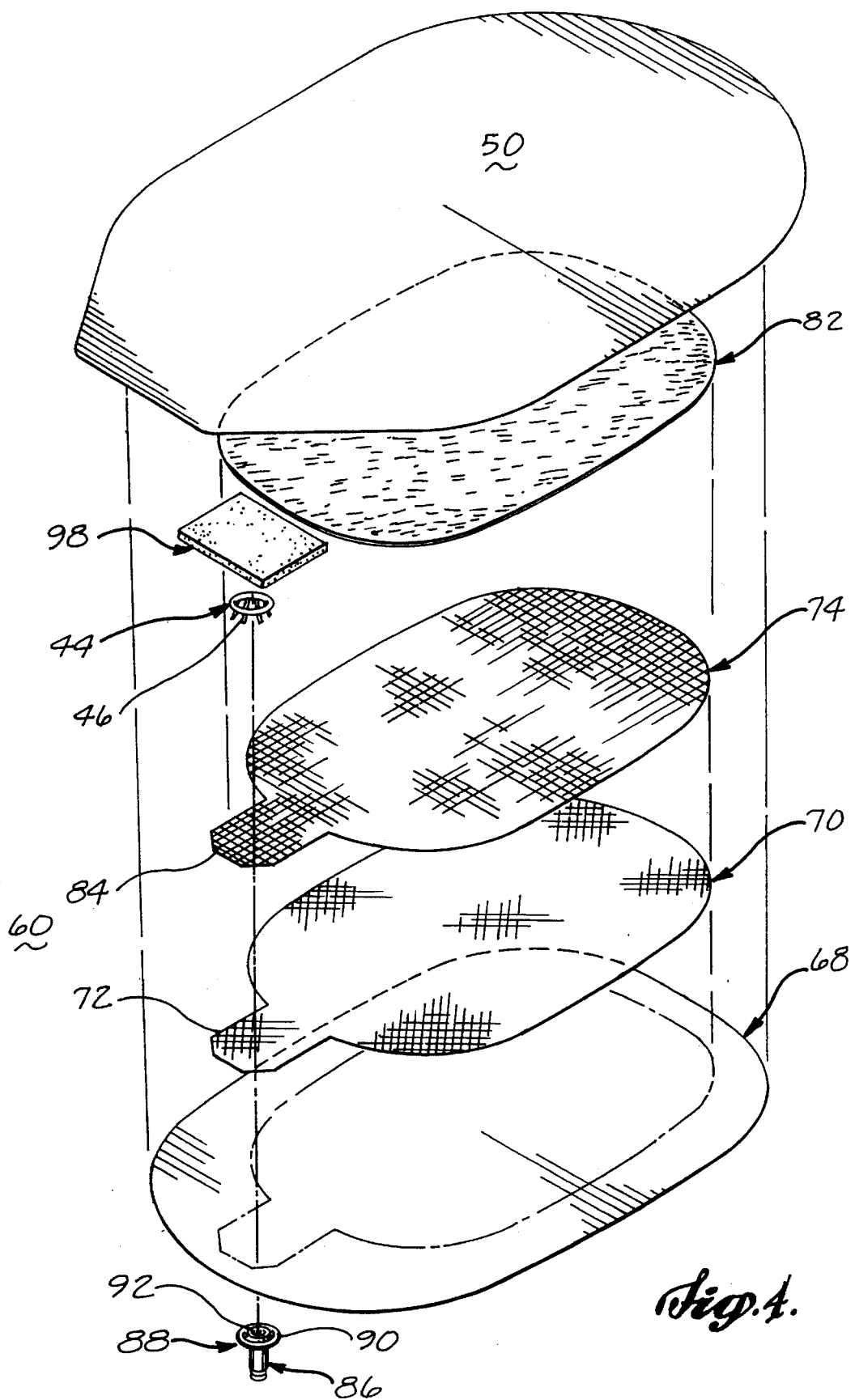
FIG. 4 is an isometric exploded view of an alternative embodiment of an electrode in accordance with the present invention.

Another alternative embodiment of an electrode 60 formed in accordance with the present invention is shown in FIG. 4. FIG. 4 illustrates electrode 60 in an exploded format.

Electrode 60 includes several layers of material. Generally flat backing layer 68 is the first layer opposite the patient-facing side of electrode 60. In this illustrated embodiment, backing layer 68 is more-or-less oval in shape, and is formed according to the same requirements as backing layer 18 in a previously described embodiment. Namely, backing layer 60 may be formed of any thin, flexible, nonwetable material that is substantially electrically nonconductive. The same types of materials suitable for forming backing layer 18 of a previously described embodiment, are suitable for forming backing layer 68 of this embodiment.

Gas-permeable layer 70 is disposed adjacent backing layer 68. In this illustrated embodiment, gas permeable layer 70 has a more-or-less oval shape, corresponding to the shape of backing layer 68, but smaller in dimension. A peninsula portion 72, having a generally rectangular shape with deeply beveled corners, centrally projects from one end of gas-permeable layer 70. The longitudinal axis of peninsula portion 72 lies generally along the longitudinal axis of gas-permeable layer 70.

Materials suitable for forming gas-permeable layer 70 include any material that is substantially permeable to gases, which can be formed into a thin, flexible sheet. The materials suitable for forming gas-permeable layer of a previously described embodiment are suitable for forming gas-permeable layer 70 of this embodiment. Preferably, gas-permeable layer 70 is formed from non-woven polyester.

A conductive layer 74, having a shape substantially identical to gas-permeable layer 70, is disposed between gas-permeable layer 70 and patient 12. Conductive layer 74 is formed of any thin, flexible material, that is a good electrical conductor, which is permeable to gases. Preferably, conductive layer 74 is formed of a thin, flexible metal mesh that is permeable to gases.

The preferred method of making electrode 60 is to first adhere gas permeable layer 70 to a conductive sheet 74. Preferably, the adhesive used is a hypoallergenic acrylic. From this assembly, conductive layer 74 and gas-permeable layer 20 are cut out with a die as an assembled unit, such that each of these layers have a substantially identical shape. Then gas-permeable layer 70 of this assembly is adhered to backing layer 68, preferably with a hypoallergenic acrylic adhesive.

FIG. 5 shows a view of an electrode 70 from the patient-facing side of the electrode. As shown in FIGS. 4 and 5, gas-permeable layer 70 and conductive layer 74 are arranged centrally upon backing layer 68. Referring to FIG. 5, backing layer 68 has larger dimensions than gas-permeable layer 70 and conductive layer 74. Thus, when these items are positioned one atop another, centrally upon the backing layer 78, an outer annular lip 80 of the backing layer 68 extends beyond these other items.

Preferably, when gas-permeable layer 70 is adhered to backing layer 68, the entire patient-facing side of backing layer 68 is coated with a hypoallergenic acrylic adhesive. Thus, even annular lip 80 is covered with the hypoallergenic acrylic adhesive. As explained in more detail below, the hypoallergenic acrylic adhesive coating on annular lip 80 helps to adhere electrode 60 to the skin of patient 12.

In this alternative embodiment, after backing layer 68, gas-permeable layer 70, and conductive layer 74 have been assembled together, an impedance-decreasing layer 82 is applied to a portion of the patient-facing sides of conductive layer 74 and the backing layer 68. As shown in FIG. 5, conductive layer 74 includes a peninsula portion 84, substantially identical in shape to peninsula portion 72 of gas-permeable layer 70. Impedance-decreasing layer 82 covers the entire surface of conductive layer 74, except for peninsula portion 84. More particularly, impedance-decreasing layer 82 covers only the base of peninsula portion 84.

Additionally, impedance-decreasing layer 82 covers an annular strip 83, surrounding the main body portion of conductive layer 74. Thus, a portion of the annular lip 80 of backing layer 68 is covered with the impedance-decreasing layer 82. Impedance-decreasing layer 82 comprises the same materials as impedance-decreasing layer 32 of a previously described embodiment.

Turning to FIG. 4, a post 86 mounts to the non-patient facing-side of backing layer 68, more-or-less centrally above peninsula portion 84 of conductive layer 74, post 86 being electrically connected to conductive layer 74. Post 86 may be electrically connected to conductive layer 74 in any conventional manner, such as by soldering, riveting, or other similar methods.

In this alternative embodiment, post 86 is electrically connected to conductive layer 74 as follows. Post 86 is formed with an enlarged base 88 having a lower rim 90 surrounding a centrally projecting column 92. Post 86 is positioned with base 88 adjacent backing layer 68. A prong ring 44 is positioned opposite base 88 of post 86, on the other side of conductive layer 74. Prong ring 44 includes a plurality of inwardly projecting teeth 46, that are bent at an angle to project towards the conductive layer 74. Post 86 is fastened to electrode 60 by teeth 46 of prong ring 44 penetrating though conductive layer 74, gas-permeable layer 70 and backing layer 68, and projecting into the space between rim 90 and column 92 of post 86.

When teeth 46 have penetrated through these items, teeth 46 are bent outward and downward, such that rim 90 of post 86 is clamped between teeth 46 and the annular outer portion of prong ring 44. Further, backing layer 68, gas-permeable layer 70, and conductive layer 74 are all forced snugly against base 88 of post 86. Electrical connection between post 86 and conductive layer 74 is provided by physical contact of engagement ring 44 with conductive layer 74, and physical contact of teeth 46 with post 86.

Preferably post 86 is formed of cartridge brass and coated with tin. When post 86 is formed of at least one metal different than the metal foil comprising conductive layer 74, impedance-decreasing layer 82 is not applied to the conductive layer 74 in the vicinity of post 86 or prong ring 44 to inhibit galvanic corrosion, as in this preferred embodiment.

Insulative pad 98 is adhered to conductive layer 74, opposite post 86, on the patient facing-side of conductive layer 74. Insulative pad 98 covers the portion of conductive layer 74 that is not coated with the impedance-decreasing layer 82. A portion of backing layer 68 is also covered by the insulative pad 98. Insulative pad 98 may be made of any thin, flexible material of high dielectric strength, such as polyethylene foam.

The purpose of insulative pad 98 is to prevent burning of the patient's skin in the event that prong ring 44 becomes electrically disconnected from conductive layer 74. For example, metal foil comprising conductive layer 74 could break away from the periphery of prong ring 44, or other events could occur to break electrical connection between prong ring 44 and conductive layer 74. In which case, if insulative pad 98 was not included with electrode 60 as described above, all of the electric current from medical electronic equipment 16 would flow into patient 12 through the relatively small area bounded by prong ring 44, resulting in a high current density and likely burning of patient 12. Insulative pad 98 protects against this occurrence.

Preferably, insulative pad 98 is adhered over conductive layer 74 with a hypoallergenic acrylic adhesive. Additionally, preferably the patient-facing side of insulative pad 98 is coated with a hypoallergenic acrylic adhesive to aid in adhering electrode 60 to patient 12.

Electrodes 60 are packaged with a protective liner 50 as shown in FIG. 4 (the protective liner 50 is not shown in FIG. 5). Protective liner 50 is releasably attached to electrode 60, as described previously with another embodiment.

In practice, electrode 60 is pressed against patient 12, after the protective liner 50 has been removed, with the impedance-decreasing layer 82 adjacent patient 12. The impedance-decreasing layer 82 is gummy and thus aids in adhering electrode 60 to the patient 12. Further, annular lip 80 of backing layer 68, and the patient-facing side of insulative pad 98 is preferably coated with a hypoallergenic acrylic adhesive. Thus, the adhesive also helps in adhering electrode 60 to patient 12.

Electrodes 60 are generally used in pairs. One electrical lead 14 attaches to post 86 of one of electrodes 60, and another electrical lead attaches to post 86 of other electrode 60. When current is applied to electrodes 60, impedance-decreasing layer 82 disposed between conductive layer 74 and patient 12 aids in making good electrical contact between the patient 12 and the electrode 60.

If impedance-decreasing layer 82 begins to hydrolyze, the bubbles of gas vent through the mesh forming conductive layer 74. This prevents the bubbles from forming pockets of gas between conductive layer 74 and patient 12. Thus, good electrical contact is maintained between electrode 60 and patient 12.

From conductive layer 74, the bubbles enter gas-permeable layer 70, whereupon the bubbles vent to the environment through the peninsula portion 72 of the gas-permeable layer 70. More specifically, impedance-decreasing layer 82 extends in an annular strip 83 from conductive layer 74 to backing layer 68. Since impedance-decreasing layer 82 has a width greater than the width of gas-permeable layer 70, bubbles generally cannot escape from the edge of gas-permeable layer 70 in areas that border on annular strip 83. In other words, the impedance-decreasing layer 82 tends to seal the edges of gas-permeable layer 70.

However, the majority part of peninsula portion 72 of gas-permeable layer 70 does not border on the annular strip 83. Thus, the bubbles vent through the peninsula portion 72 to the environment, as indicated by the arrows 102 shown in FIG. 2. (Peninsula portion 72 of gas permeable layer 70 is disposed under peninsula portion 84 of conductive layer 74.)

While the preferred embodiment of the invention has been illustrated and described, it will be appreciated that various changes can be made therein without departing from the spirit and scope of the invention. For example, the gas-permeable layers 20 and 70 of the previously described embodiments could be replaced with a thin flexible sheet incorporating a plurality of channels or creases. Bubbles would collect in the channels and be directed to a vented part of the electrode.

Alternatively, the conductive layers of the above-described embodiments could incorporate channels or creases, allowing for gas-permeable layers 20 and 70 to be eliminated. The bubbles would collect in the channels in the conductive layers 24 and 74, and be directed to a vented portion of the electrode.

Another modification within the scope of the present invention, is that the conductive layers could be replaced with a porous material having a conductive ink printed upon the patient-facing side of the conductive layer. The porous material could be a plastic mesh, an open cell foam, a nonwoven material, or other material permeable to gases.

In the preferred embodiment incorporating impedance-decreasing layer 32, annular strip 33 of the impedance-decreasing layer could be eliminated. Thus, gas could vent from the entire periphery of the gas-permeable layer 20, rather than just from the peninsula portion 22.

A further possible modification of this preferred embodiment within the scope of the present invention, is that post 36 could be soldered to conductive layer 24, with bore holes being provided in support sheet 26, gas-permeable layer 20 and backing layer 18, in which post 36 would penetrate upwardly through the bore holes.

In view of these and other alterations, substitutions, replacements and modifications that could be made by one of ordinary skill in the art, it is intended that the scope of letters patent granted hereon be limited only by the definitions of the appended claims.

The embodiments of the invention in which an exclusive property or privilege is claimed are defined as follows:

1. An electrode for placement upon the skin of a patient to deliver electrical pulses from medical electronic equipment to the patient, the electrode comprising:
   (a) an electrically conductive layer having a skin-facing side and an upper side
   (b) an impedance-decreasing layer disposed on the skin-facing side of the conductive layer;
   (c) a substantially electrically nonconductive backing layer disposed on the upper surface of the conductive layer, the backing layer being substantially impermeable to the impedance-decreasing layer; and
   (d) vent means for venting gas formed between the impedance-decreasing layer and the conductive layer.

2. The electrode of claim 1, wherein the conductive layer is permeable to gases.

3. The electrode of claim 2, wherein the vent means comprises a gas-permeable layer between the conductive layer and the backing layer.

4. The electrode of claim 3, wherein the impedance-decreasing layer includes an outer periphery, and the vent means includes a portion of the gas-permeable layer extending beyond the periphery of the impedance-decreasing layer.

5. The electrode of claim 1, wherein the conductive layer is perforated.

6. The electrode of claim 1, wherein the conductive layer comprises a mesh.

7. The electrode of claim 1, further comprising a gas-permeable layer positioned between the conductive layer and the backing layer.

8. The electrode of claim 7, wherein the gas-permeable layer comprises a nonwoven material.

9. The electrode of claim 8, wherein the nonwoven material comprises polyester.

10. An electrode for placement upon the skin of a patient to deliver electrical pulses from medical electronic equipment to the patient, the electrode comprising:
    (a) an electrically conductive layer having a skin-facing side and an upper side, the electrically conductive layer being permeable to gases;
    (b) an impedance-decreasing layer disposed on the skin-facing side of the conductive layer; and
    (c) a substantially electrically nonconductive backing layer disposed on the upper surface of the conductive layer, the backing layer being substantially impermeable to the impedance-decreasing layer.

11. The electrode of claim 10, wherein the backing layer comprises a material permeable to gases.

12. The electrode of claim 10, further comprising a gas-permeable layer between the conductive layer and the backing layer, the gas-permeable layer including a vented portion for permitting gaseous exchange between the gas-permeable layer and the environment.

13. The electrode of claim 12, wherein the gas-permeable layer comprises a nonwoven material.

14. The electrode of claim 12, wherein the nonwoven material comprises polyester.

15. The electrode of claim 10, wherein the impedance-decreasing layer includes an outer periphery, and the gas-permeable layer includes a portion extending beyond the periphery of the impedance-decreasing layer.

16. The electrode of claim 10, wherein the impedance-decreasing layer includes an outer periphery, and the conductive layer includes a portion extending beyond the periphery of the impedance-decreasing layer.

17. The electrode of claim 16, further comprising an electrical coupler connected to the portion of the conductive layer extending beyond the periphery of the impedance-decreasing layer for electrically connecting the conductive layer to the medical electronic equipment.

18. The electrode of claim 10, wherein electrical coupling between the conductive layer and the skin of the patient substantially only occurs through the impedance-decreasing layer.

* * * * *